United States Patent [19]

Watanabe et al.

[11] 4,188,534
[45] Feb. 12, 1980

[54] INFRARED GAS ANALYZER

[75] Inventors: Atsuo Watanabe; Hidenori Ishizawa; Masahiro Uno, all of Kawasaki, Japan

[73] Assignee: Fuji Electric Co., Ltd., Kawasaki, Japan

[21] Appl. No.: 898,045

[22] Filed: Apr. 20, 1978

[51] Int. Cl.² .......................................... G01N 21/26
[52] U.S. Cl. .................................................. 250/345
[58] Field of Search ............... 250/343, 344, 345, 373; 356/51, 201, 204, 206

[56] References Cited

U.S. PATENT DOCUMENTS

| | | | |
|---|---|---|---|
| 3,193,676 | 7/1965 | Smart | 250/345 |
| 3,851,176 | 11/1974 | Jeunehomme et al. | 250/345 X |
| 3,916,195 | 10/1975 | Burch et al. | 250/345 |
| 4,004,146 | 1/1977 | Blunck | 250/345 |
| 4,008,394 | 2/1977 | Risgin et al. | 250/345 |

Primary Examiner—Davis L. Willis
Attorney, Agent, or Firm—Sughrue, Rothwell, Mion, Zinn and Macpeak

[57] ABSTRACT

The performance of a single light source parallel chambertype infrared gas analyzer is improved by enlarging the single inlet opening of the light divider and by positioning the light source such that the center axes of the two light passages of the light divider intersect at the light source. The assembly and alignment adjustment of the various functional components of the analyzer is also simplified.

8 Claims, 16 Drawing Figures

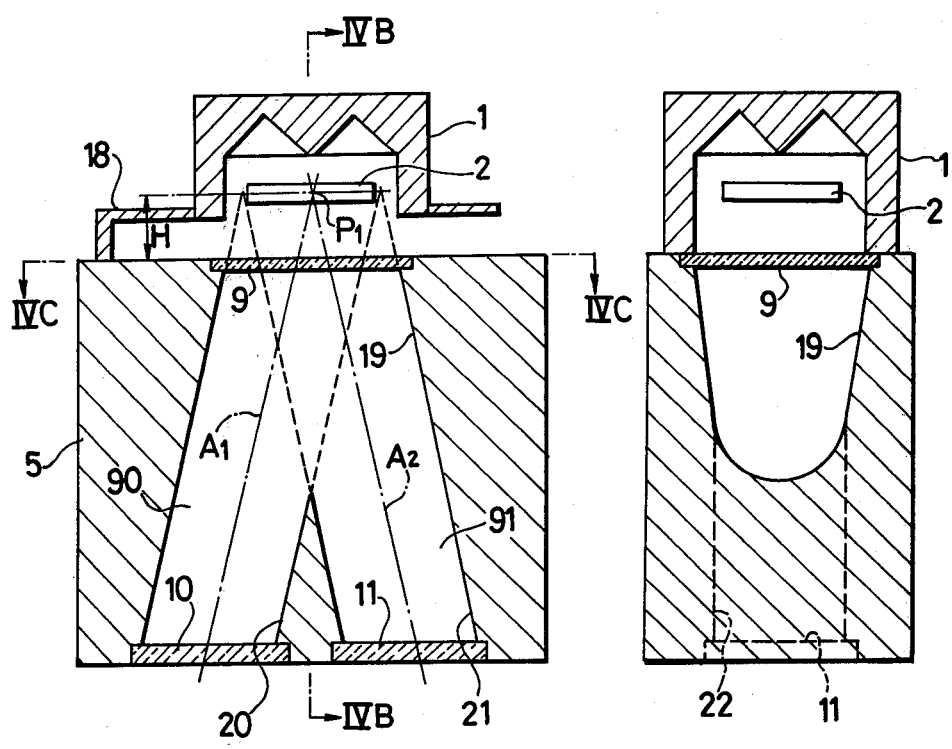

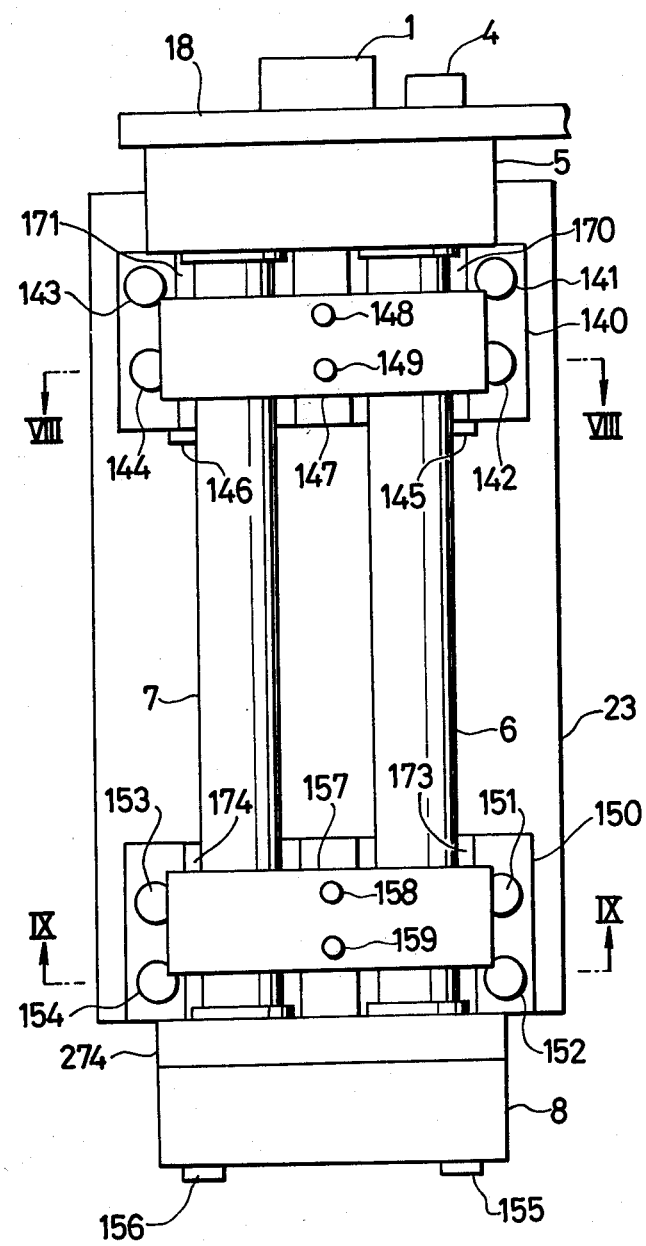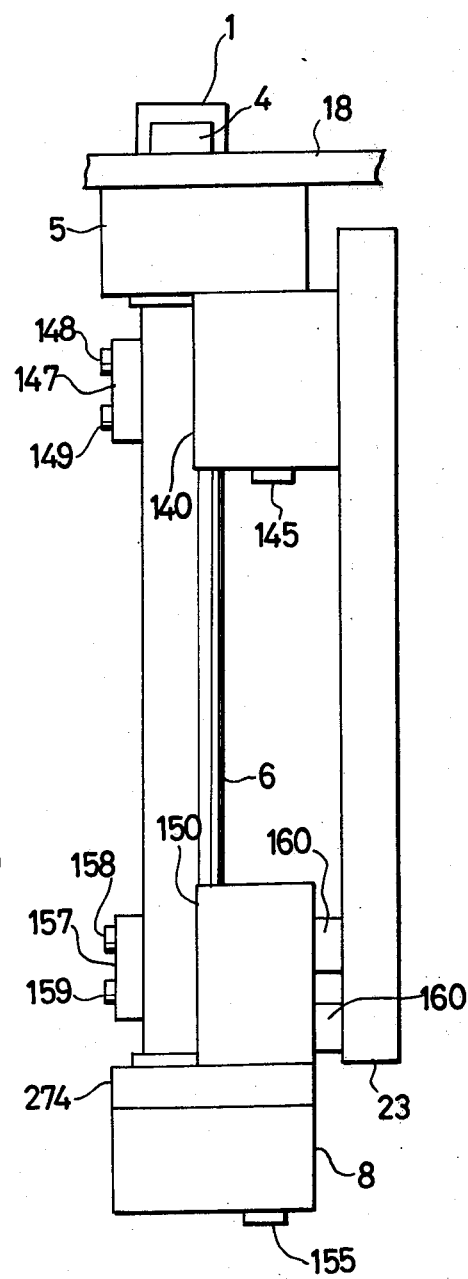

INFRARED GAS ANALYZER

BACKGROUND OF THE INVENTION

The present invention relates to an optical analyzing apparatus having an optical system including a light source portion, a cell portion and a detector portion.

The optical analyzing apparatus such as, for example, an infrared gas analyzing apparatus, has been used for analyzing various gases by utilizing the difference in infrared absorption between the test gas and a reference gas. As shown in FIG. 1, a typical infrared gas analyzing apparatus comprises a light source portion which includes a light source chamber 1, a chopper chamber 18 containing a chopper plate 3 rotated by a motor 4 and a light dividing chamber 5, a cell portion including a reference cell 6 and a sample cell 7, and a detector portion 8 including a pair of detector chambers 8A and 8B.

It is possible to use two light sources rather than the single source and light divider of FIG. 1. However, if two light sources are used, an unbalance between the light sources may be a problem, causing a drift of the null point of the system. On the other hand, there is no such drift problem in the single light source type due to the fact that it uses only one source, the infrared light from which is divided into two beams in the light dividing chamber. Therefore, the single light source type gas analyzer has been widely used.

The light divider 5 has an inlet window facing the light source chamber 2 sealed with a sealing plate 9 of an infrared transparent material and also has a pair of outlet windows which are sealed by plates 10 and 11 of an infrared transparent material, respectively. Light passages connecting the inlet window and the respective outlet windows have circular cross sections of the same diameter. The passages are filled with a gas such as nitrogen gas which does not absorb the infrared ray. If the sample gas contains an interfering gas component which will absorb the infrared ray at a wavelength to be absorbed by an object gas component, the passages can be filled with the interferring gas.

The two beams are guided through the passages into the cell portion comprising a reference cell 6 and a measuring cell 7. One of the beams passes through the reference cell 6 as a reference beam and the other passes through the measuring cell 7 as a measuring beam. Opposite ends of the reference cell 6 are sealed with light transparent windows 14 and 15 and, as in the light divider 5, the cell 6 is filled with a gas such as pure nitrogen gas which does not absorb the intended wavelength of the infrared ray. The measuring cell 7 is also sealed at opposite ends with light transparent windows 12 and 13 and is provided at the upstream side thereof with a gas inlet port 7A for in introducing the measuring or sample gas and at the downstream side thereof with an outlet port 7B to establish a flow of the measuring gas containing the gas component to be analyzed. The measuring beam is absorbed by the gas component, the amount of absorption being dependent upon the concentration thereof.

The beams passed through the respective cells are introduced into the detector portion. The detector portion is a gas filled detector 8 which comprises detecting chambers 8A and 8B sealed with light transparent windows 16, 17 and filled with a pure gas of the same kind as the gas component of the sample gas which is to be analyzed, so that the detector chambers 8A and 8B are heated to different temperatures according to intensities of the measuring beam and the reference beam passed thereto, respectively. The chambers 8A and 8B are communicated with each other by a communication portion 8C in which a pair of heat-sensitive elements 8D and 8E are disposed. The elements 8D and 8E, together with a pair of resistors (not shown) constitute a bridge circuit which is heated to a temperature higher than the ambient temperature by supplying a d.c. current therethrough. When the gases in the chambers 8A and 8B are heated to different temperatures according to the different intensities of the beams, a flow of the gas occurs through the communicating portion 8C from the chamber 8B to 8A because the gas in the chamber 8B is heated to a higher temperature than that in chamber 8A. The gas flow is converted by the elements 8D and 8E into an electric signal indicative of the amount of the particular gas component contained in the sample gas.

FIG. 2A shows in cross section the light source portion of FIG. 1 in more detail and FIG. 2B is a cross section taken along IIB—IIB of FIG. 2A. In FIG. 2A the chopper plate 3 of FIG. 1 is omitted for convenience in explanation.

In FIG. 2A, the opening of the light source chamber 1 faces the sealing plate 9 in the inlet 19 of the light divider 5. The inside surface of the light source chamber 1 behind the light source 2 is formed with a plurality of conical mirrors K1 and K2 which effectively reflect the light emitted from the rear side of the light source 2 back to the light divider 5.

The light divider 5 is formed with a pair of straight passages 60 and 61, each having one end connected together at the inlet 19 and the other ends of which form separate outlets 21 and 22 of the divider 5, respectively, forming a generally V-shaped space. The light passages 60 and 61 have the same diameter D and optical axis A1 and A2, respectively. A cross point P of the axes $A_1$ and $A_2$ corresponds to the center of the sealing plate 9.

In order to increase the amount of light emitted from the light source portion and introduced into the divider 5, to thereby improve the efficiency of the analyzer, it is necessary to either raise the temperature of the light source 2 or increase the light emitting area of the light source 2, according to Stefan-Boltzmann's law. Raising the light source temperature may cause the life of the light source to be shortened. Therefore, it is preferable to enlarge the light source. However, even if the light emitting area of the light source 2 is enlarged, the effective light emitted by the enlarged light source and guided into the light passages 60 and 61 may not be increased proportionally to the increase of the light emitting area of the light source. In other words, the effective light cannot be increased proportionally to the electric power consumed, resulting in inefficiency. Therefore, it is highly desirable to provide a more efficient way of increasing the effective light.

A further disadvantage of the conventional infrared gas analyzer can be understood from FIG. 3.

In FIG. 3, the light source portion including the chopper mechanism 3, 4, 18, and the light source chamber 1, the light divider 5, the measuring cell portion including the reference cell 6 and the measuring cell 7 and the detector portion 8 are independently mounted on a base plate 23. The divider 5 to which is mounted the light source chamber 1 and the chopper mechanism is fixed to a supporting plate 24 by suitable means (not shown) and the supporting plate 24 is fixedly secured to the base plate 23 by means of mounting screws 27.

The reference cell 6 and the measuring cell 7 are supported in parallel between a supporting plate 28 and a pair of supporting members 25 and 26 by screws 35 and 36 and the supporting members are fixedly secured to the base plate 23 by screws 31, 32, 33 and 34. Finally, the detector portion 8 is suitably supported by a supporting member 29 which is fixedly secured to the base plate 23 by screws 37, 38, 39 and 40.

In order to perform the analysis effectively, it is necessary to align the optical axes of the light divider 5, the cells 6 and 7 and the detector 8. However, with this arrangement of the functional components, it is very difficult to obtain an exact alignment of the components due to the independent securings for each. Furthermore, even if the exact alignment is achieved, the components may be disposed due, for instance, to temperature variations causing the analysis to be inaccurate and, therefore, the components have to be realigned.

SUMMARY OF THE INVENTION

An object of the present invention is to improve the performance of the single light source type infrared gas analyzer.

Another object of the present invention is to provide an improved light divider to be used in the infrared gas analyzer which enables the light emitting area of the light source to be increased efficiently.

A further object of the present invention is to provide an improved arrangement of the infrared gas analyzer by which the various functional components of the latter can be easily aligned.

A still further object of the present invention is to provide an improved infrared gas analyzer which is easily reassembled with accurate alignment.

These and other objects are achieved by providing a light divider having an enlarged inlet aperture and spaced from the light source so that the center axes of the two light passages in the light divider intersect at the light source. Assembly and adjustment of the various components of the gas analyzer is made simple by supporting the measuring and reference cells between a pair of V-blocks and mounting the light source portion and detector portion on the V-blocks.

BRIEF DESCRIPTION OF THE DRAWINGS

FIG. 4A is a similar cross section to that in FIG. 2A showing an embodiment of the present invention.

FIG. 4B is a cross section taken along with the line IVB—IVB in FIG. 4A.

FIG. 4C is a view similar to FIG. 2C of the inlet and outlet openings of the light divider in FIG. 4A.

FIG. 6 is a plan view of the arrangement of the infrared gas analyzer according to the present invention.

FIG. 7 is a side view of the arrangement in FIG. 6.

DETAILED DESCRIPTION OF THE PREFERRED EMBODIMENTS

In FIGS. 4A to 4C which show the improved light source portion of the infrared gas analyzer according to the invention, the inlet opening portion of the light divider 5 is increased in area and the cross point $P_1$ of the optical axes $A_1$ and $A_2$ of the light passages is set at the center of the light source 2.

Figure 1:
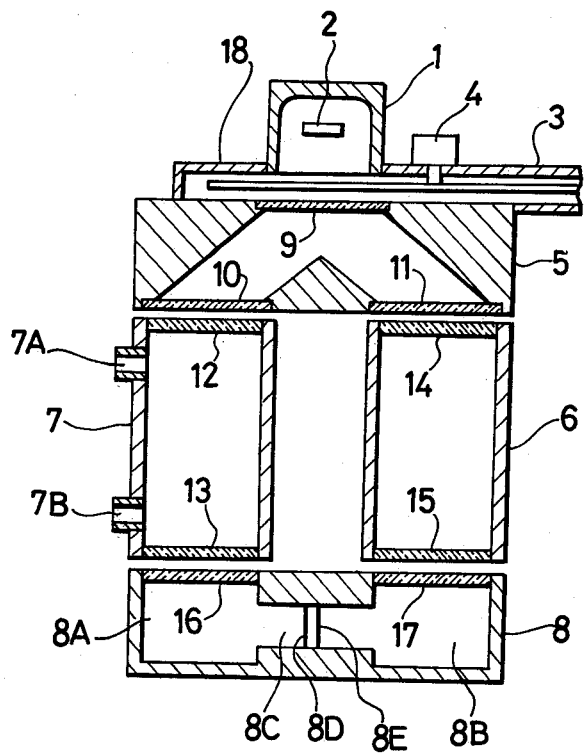
FIG. 1 shows, schematically in cross section, the conventional infrared gas analyzer of the single light source type already described.
Figure 3:
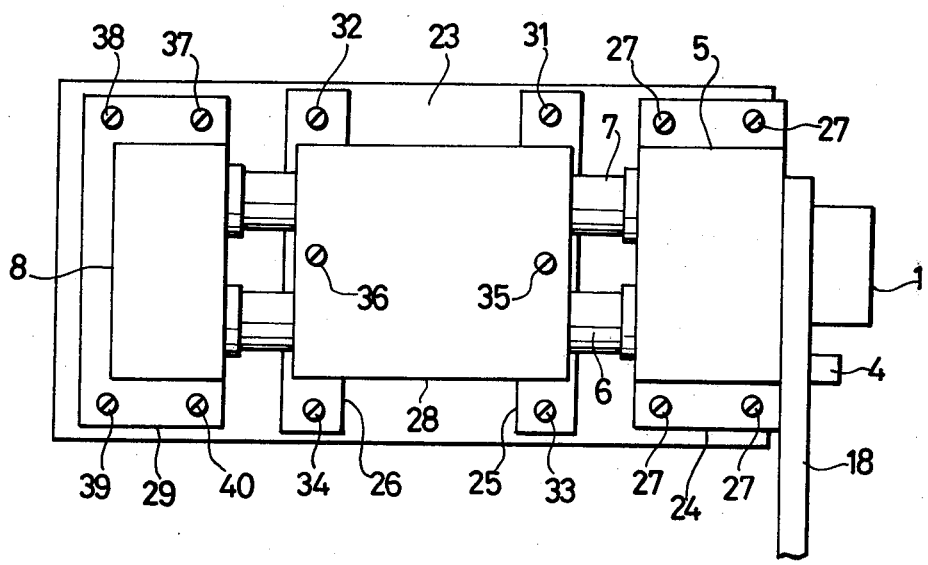
FIG. 3, already described, is a top plan view of the infrared gas analyzer in FIG. 1, showing the mountings of the various components thereof.
Figure 2A:
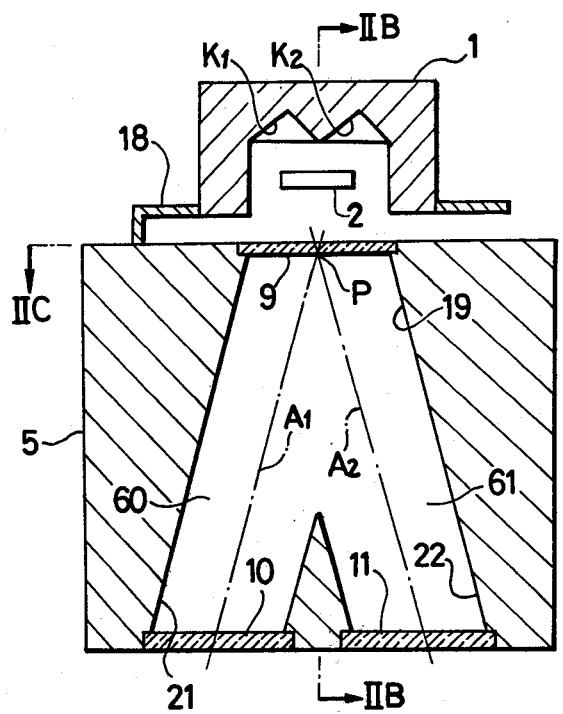
FIG. 2A shows the light source portion of the infrared gas analyzer in FIG. 1 in detail.
Figure 2B:
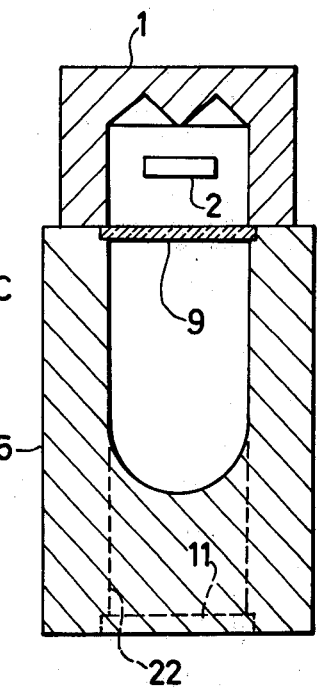
FIG. 2B is a cross section taken along a line IIB—IIB in FIG. 2A.
Figure 2C:
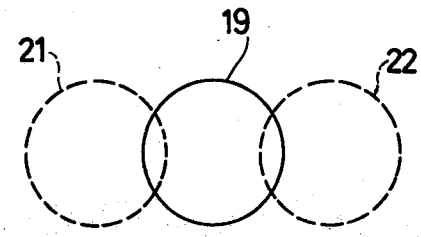
FIG. 2C is a projection in a single plane of the inlet opening and the outlet openings of the light divider used in the light source portion.
Figure 5:
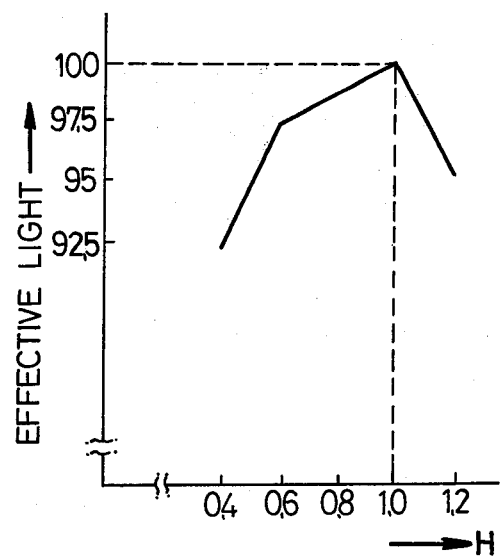
FIG. 5 is a graph showing the relation between the light source position and the effective light.

Assuming the distance H between the light source 2 and the inlet sealing window 9, the relation between the distance H and the effective light is shown in FIG. 5. The value of 1.0 H is the distance at which the light source 2 is set at the same level as the cross point P as in FIG. 4A, the amount of the effective light showing a peak at the unity distance.

Therefore, the passages each having diameter D are formed so that the axes $A_1$ and $A_2$ thereof are crossed at the center $P_1$ of the light source 2. The openings of these passages at the inlet side of the divider 5 are partially overlapped as shown by thin dotted lines in FIG. 4C. The inlet side thereof may be cut with a tapered drill, the diameter $D_1$ of the thick portion of the drill being equal to the diameter of a circle inscribed by the openings of the passages at the inlet sides thereof as shown in FIG. 4C. The degree of the taper of the drill should be selected such that the tapered wall portion of the drilled hole is smoothly connected to the walls of the passage holes as shown in FIG. 4B.

By forming the inlet hole having a diameter $D_1$, the hatched portions B in FIG. 4C are cut away. This causes the amount of the effective light introduced into the light divider 5 to be increased by 20% over the light amount which would be obtained without forming the tapered hole.

FIG. 6 is a plan view of the whole arrangement of the infrared gas analyzer equipped with the light source portion improved according to the present invention, and FIG. 7 is a side view of the analyzer in FIG. 6.

In FIGS. 6 and 7, the light source portion is previously assembled by suitably stacking the light source chamber 1, the chopper chamber 18 and the light divider 5. A clamping block 140 is also secured to the base plate 23 by screws 141, 142, 143 and 144. The light source portion is secured to the upper side surface of the upper clamping block 140 by a pair of screws 145 and 146.

A lower clamping block 150 is secured to the base plate 23 by screws 151, 152, 153 and 154 through respective spacers 160. The detector portion 8 is secured to the lower side surface of the lower clamping block 150 by a pair of screws 155 and 156. The clamping block 140 has a pair of parallel V grooves 170 and 171 and the clamping block 150 has a pair of parallel V grooves 173 and 174, the distance between the grooves 173 and 174 being the same as that between the grooves 170 and 171 of the clamping block 140. The securing of the clamping blocks 140 and 150 to the base plate 23 is such that the groove pair of the block 140 are aligned with those of the block 150.

The reference cell 6 and the measuring cells 7 are placed in parallel on the grooves 170 and 173 and the grooves 171 and 174, respectively. The fastening of the cells 6 and 7 to the grooves 170, 173 and 171, 174 is performed by positioning a plate member 147 above the clamping block 140 and a plate member 157 above the block 150 and tightening them to their respective blocks by screws 148, 149 and 158, 159, respectively.

Figure 8A:
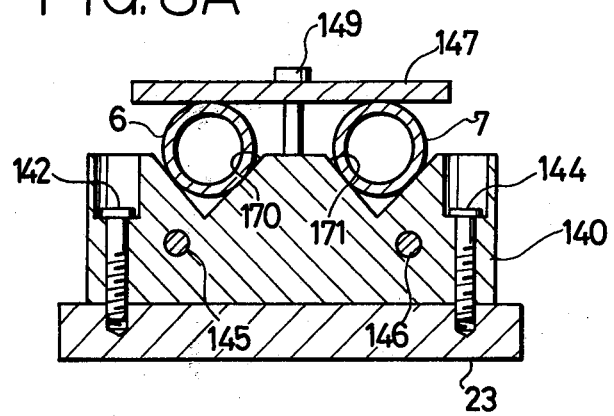
FIG. 8A is a cross section taken along a line VIII—VIII in FIG. 6.
Figure 8B:
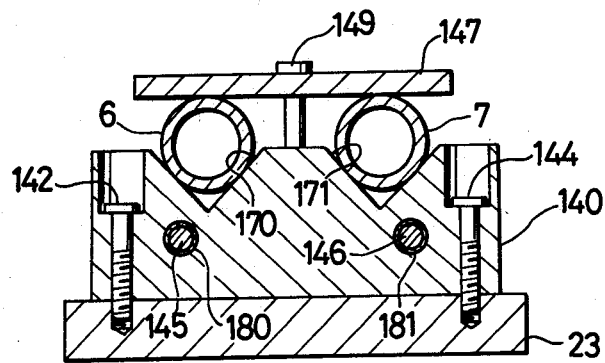
FIG. 8B is a view similar to that in FIG. 8A, showing a modification thereof.

FIG. 8A is a cross section taken along a line VIII—VIII in FIG. 6 showing the light source portion directly connected to the clamping block 140 by the screws 145 and 146. FIG. 8B is a similar cross section to that in FIG. 8A, the only difference being that the securing of the light source portion to the clamping block 140 is indirectly performed through a pair of positioning collars 180 and 181. With the use of the collars in connecting the light source portion to the clamping block 140, position adjustment of the light source is made easier than with the direct connection in FIG. 8A.

Figure 9C:
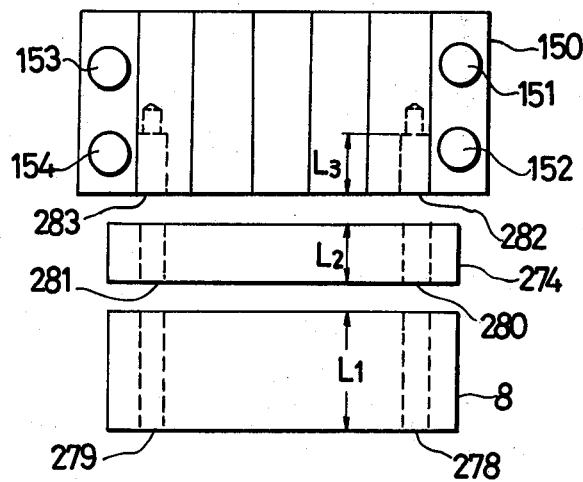
FIG. 9C shows the structure in FIG. 9A in a disassembled state.
Figure 9A:
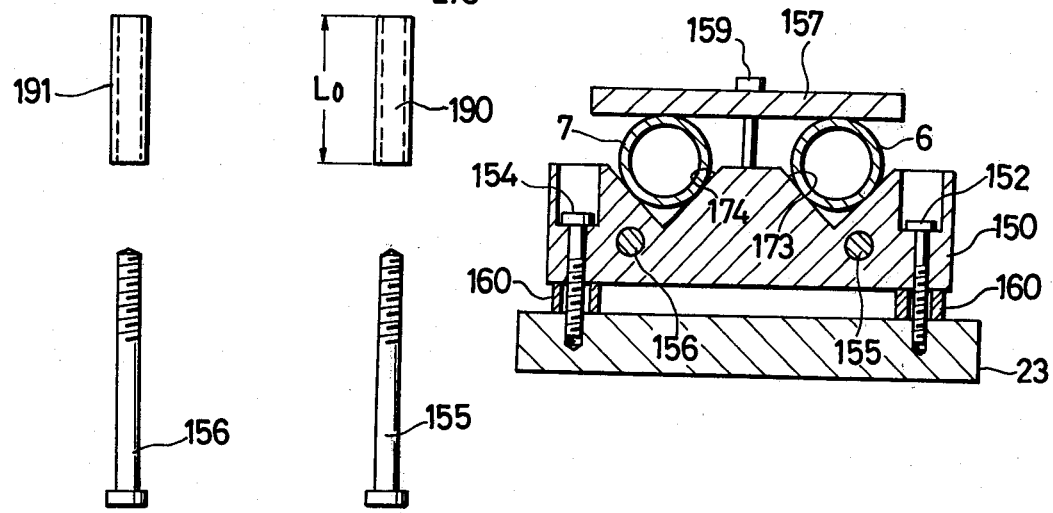
FIG. 9A is a view similar to that in FIG. 8A, showing another embodiment of the present invention.
Figure 9B:
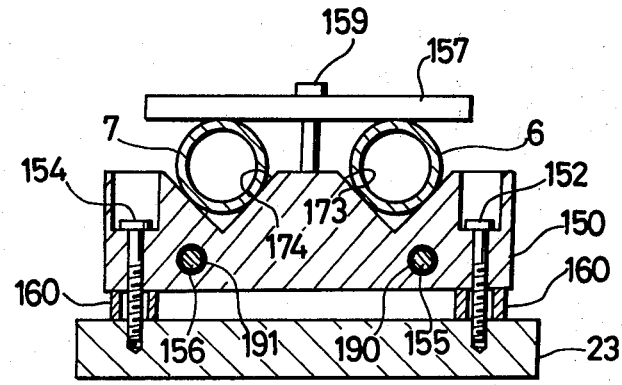
FIG. 9B is a view similar to that in FIG. 8B, showing another embodiment of the present invention.

FIG. 9A is similar to FIG. 8A and shows a cross section taken along a line IX—IX in FIG. 6 and FIG. 9B is similar to FIG. 8B showing a modification of FIG. 9A. FIG. 9C shows in a disassembled state, the detector 8 of FIG. 6 and the clamping block 150 in FIG. 9B. In order to accomodate the positioning collars 190 and 191, the detector 8 and a filter or light amount regulator 274, if required, are formed with through-holes 278 and 279, and 280 and 281, respectively. The length of the collar is selected such that it is longer than $L_2+L_3$ and shorter than $L_1+L_2+L_3$ wherein $L_1$ is the length of the detector 8, $L_2$ is the length of the regulator 274 and $L_3$ is the depth of the holes 282 and 283.

As will be clear from FIGS. 9A and 9B, the securing of the clamping block 150 to the base plate 19 is accomplished by using spacer rings 160 of an elastic or resilient material such as rubber through which the screws 151 to 154 are inserted.

As described hereinabove, according to the present invention the amount of the effective light to be introduced into the light divider is much increased and the assembling of the various functional components, including the light source portion, becomes much easier. Furthermore, even when it is necessary to rearrange the components for some reason, it can be performed without difficulty.

What is claimed is:

1. An infrared gas analyzing device of the type comprising a light source portion, a cell portion having measuring and reference cells and a detector portion and wherein said light source portion comprises a light source and a light divider, the latter having an inlet opening in a surface facing said light source for receiving light emitted from said light source and first and second light passages having center axes and communicating with said inlet opening for supplying separate beams of light to said measuring and reference cells, respectively, wherein the improvement comprises:
the center axes of said first and second light passages intersecting at said light source.

2. An infrared gas analyzer according to claim 1, wherein said inlet opening is a tapered hole having its largest diameter at the surface of said light divider, the diameter of said inlet opening at said surface being at least as large as the longest dimension of the combined projections of said light passages in the plane of said surface.

3. An infrared gas analyzer according to claim 1 or 2, wherein said measuring and reference cells are separate cylindrical members, said device further comprising:
a first clamping block for supporting said cylindrical members at one end;
first securing means for securing said light source portion to said first clamping block in alignment with said cylindrical members;
a second clamping block for supporting said cylindrical members at their other ends; and
second securing means for securing said detector portion to said second clamping block in alignment with said cylindrical members.

4. An infrared gas analyzer device according to claim 3, wherein said first clamping block includes first and second V-shaped grooves, said second clamping block includes third and fourth V-shaped grooves axially aligned with said first and second grooves, resepctively, and wherein said first cylindrical member is supported in said first and third grooves and said second cylindrical member is supported in said second and fourth grooves.

5. An infrared gas analyzing device of the type comprising a light source portion, a cell portion having measuring and reference cells and a detector portion, wherein said light source portion comprises a light source and a light divider, the latter having an inlet opening in a surface thereof facing said light source for receiving light emitted from said light source and first and second light passages having center axes and communicating with said inlet opening for supplying separate beams of light to said measuring and reference cells, respectively, wherein the improvement comprises:
said inlet opening comprising a tapered hole having its largest diameter at the surface of said light divider, the diameter of said inlet opening at said surface being at least as large as the longest dimension of the combined projections of said light passages in the plane of said surface.

6. An infrared gas analyzing device according to claim 5, wherein the center axes of said first and second light passages intersect at said light source.

7. An infrared gas analyzing device of the type comprising a light source portion having a light source and first and second light passages for providing infrared light, a cell portion comprising measuring and reference cells for passing said infrared light and a detector portion for receiving said infrared light from said measuring and reference cells, wherein the improvement comprises:
a first clamping block for supporting one end of said cell portion;
first securing means for securing said light source portion to said first clamping block in alignment with said cell portion;
a second clamping block for supporting the other end of said cell portion; and
second securing means for securing said detector portion to said second clamping block in alignment with said cell portion.

8. An infrared gas analyzing device according to claim 7, wherein said first clamping block includes first and second V-shaped grooves and said second clamping block includes third and fourth V-shaped grooves axially aligned with said first and second grooves, respectively, and wherein said measuring cell is supported in said first and third grooves and said reference cell is supported in said second and fourth grooves.

* * * * *